(12) United States Patent
Freund et al.

(10) Patent No.: US 7,470,422 B2
(45) Date of Patent: *Dec. 30, 2008

(54) METHOD FOR THE PRODUCTION OF PROPELLANT GAS-FREE AEROSOLS FROM AQUEOUS MEDICAMENT PREPARATIONS

(75) Inventors: Bernhard Freund, Gau-Algesheim (DE); Bernd Zierenberg, Bingen am Rhein (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/506,128

(22) Filed: Aug. 17, 2006

(65) Prior Publication Data

US 2007/0077207 A1    Apr. 5, 2007

Related U.S. Application Data

(63) Continuation of application No. 10/417,766, filed on Apr. 17, 2003, now abandoned, which is a continuation of application No. 09/331,023, filed as application No. PCT/EP97/07062 on Dec. 16, 1997, now abandoned.

(30) Foreign Application Priority Data

Dec. 20, 1996    (DE)    ................................. 196 53 969

(51) Int. Cl.
*A61K 9/12*    (2006.01)
*A61K 38/00*    (2006.01)
*A61M 15/00*    (2006.01)

(52) U.S. Cl. ........................... 424/45; 424/434; 424/43; 514/826; 514/642; 128/200.14

(58) Field of Classification Search ................. 424/45, 424/434, 43; 514/826, 642; 128/200.14
See application file for complete search history.

(56) References Cited

U.S. PATENT DOCUMENTS

| 5,497,944 A | 3/1996 | Weston et al. |
| 5,964,416 A | 10/1999 | Jaeger et al. |
| 5,976,573 A | 11/1999 | Kim |
| 6,150,418 A | 11/2000 | Hochrainer et al. |
| 6,455,524 B1 | 9/2002 | Bozung et al. |
| 6,491,897 B1 | 12/2002 | Freund et al. |
| 6,630,466 B2 | 10/2003 | Bozung et al. |
| 6,890,517 B2 | 5/2005 | Drechsel et al. |
| 2002/0193392 A1 | 12/2002 | Schmeizer et al. |
| 2004/0019073 A1* | 1/2004 | Drechsel et al. ............. 514/291 |
| 2004/0132761 A1 | 7/2004 | Drechsel et al. |

FOREIGN PATENT DOCUMENTS

| DE | 196 25 027 A1 | 1/1997 |
| DE | 196 20 509 A1 | 11/1997 |
| EP | 0310910 A1 | 4/1989 |
| EP | 0 370 632 B1 | 5/1990 |
| EP | 0 489 217 A1 | 6/1992 |
| JP | 4-275235 A | 9/1992 |
| JP | 5-58888 A | 3/1993 |
| JP | 8-508280 A | 9/1996 |
| JP | 10-130148 | 5/1998 |
| JP | 11-508547 | 7/1999 |
| JP | 2001-501914 A | 2/2001 |
| WO | WO 91/14468 A1 | 10/1991 |
| WO | WO 94/13262 | 6/1994 |
| WO | WO 97/01329 A1 | 1/1997 |
| WO | WO 97/12687 A1 | 4/1997 |
| WO | WO 99/07340 A1 | 1/1999 |
| WO | WO 00/23037 A1 | 4/2000 |

OTHER PUBLICATIONS

U.S. Appl. No. 09/396,673, Fruend, B et al, pending.
U.S. Appl. No. 09/497,696, Lamche, H. et al, pending.
JP 08-508280 Abstract.
JP 05-058888 Patent Abstracts of Japan.
JP 04-275235 Abstract.
JP 10-130148 Abstract.
JP 2001-501914 Abstract.
JP 11-508547 Abstract.
The Merck Index, 12th Edition. #217 and #5089, 1996.
Moren et al., "Aerosol dosage forms and formulations" Aerosols in Medicine, Principles, Diagnosis and Therapy, 2nd Edition, Chapter 13, Section 4, 1993.

* cited by examiner

*Primary Examiner*—Mina Haghighatian
(74) *Attorney, Agent, or Firm*—Michael P. Morris; Mary-Ellen M. Devlin; Timothy X. Witkowski

(57) ABSTRACT

The present invention relates to pharmaceutical preparations in the form of aqueous solutions for the production of propellant-free aerosols.

18 Claims, No Drawings

METHOD FOR THE PRODUCTION OF PROPELLANT GAS-FREE AEROSOLS FROM AQUEOUS MEDICAMENT PREPARATIONS

RELATED APPLICATIONS

This application is a continuation of U.S. Ser. No. 10/417,766, filed Apr. 17, 2003, now abandoned, which was a continuation of U.S. Ser. No. 09/331,023, filed Sep. 15, 1999, now abandoned, which is a filing under 35 U.S.C. § 371 of PCT/EP97/07062, filed Dec. 16, 1997.

BACKGROUND AND SUMMARY OF THE INVENTION

The present invention relates to pharmaceutical preparations in the form of aqueous solutions for the production of propellant-free aerosols for inhalation.

In the last 20 years, the use of dosage aerosols has become a strong part of the therapy of obstructive lung diseases, especially asthma. Usually, fluorochlorohydrocarbons are used as propellant gases. Following the recognition of the ozone damaging potential of these propellant gases, attempts to develop alternatives have increased. One alternative is the development of nebulizers, where aqueous solutions of pharmacologically active substance are sprayed under high pressure so that a mist of inhalable particles results. The advantage of these nebulizers is that they completely dispense with the use of propellant gases.

Such nebulizers are, for example, described in PCT Patent Application WO 91/14468 (the Weston Nebulizer), herein incorporated by reference. With the nebulizers described here, active ingredients solutions in defined volumes are sprayed through small jets under high pressure, so that inhalable aerosols with a mean particle size of between 3 and 10 micrometers result. A further developed embodiment of the aforementioned nebulizer is described in PCT/EP96/04351 (the Jaeger Nebulizer A). The nebulizer portrayed in FIG. 6 of PCT/EP96/04351 (the Jaeger Nebulizer B) carries the trademark Respimat®.

Usually, pharmaceuticals intended for inhalation are dissolved in an aqueous or ethanolic solution, and according to the solution characteristics of the active substances, solvent mixtures of water and ethanol may also be suitable.

Other components of the solvent are, apart from water and/or ethanol, optionally other cosolvents, and also the pharmaceutical preparation may also additionally contain flavourings and other pharmacological additives. Examples of cosolvents are those which contain hydroxyl groups or other polar groups, for example, alcohols, especially isopropyl alcohol, glycols, especially propylene glycol, polyethylene glycol, polypropylene glycol, glycol ether, glycerol, polyoxyethylene alcohols, and polyoxyethylene fatty acid esters. Cosolvents are suitable for increasing the solubility of adjuvant materials and, if necessary, active ingredients.

The proportion of dissolved pharmaceutical in the finished pharmaceutical preparation is between 0.001% and 30%—preferably between 0.05% and 3%, especially 0.01% to 2% (weight/volume). The maximum concentration of pharmaceutical is dependent on the solubility in solvent and on the dosage required to achieve the desired therapeutical effect.

All substances which are suitable for application by inhalation and which are soluble in the specified solvent can be used as pharmaceuticals in the new preparations. Pharmaceuticals for the treatment of diseases of the respiratory passages are of especial interest. Therefore, of especial interest are betamimetics, anticholinergics, antiallergics, antihistamines, and steroids, as well as combinations of these active ingredients.

It was found, in a series of examinations, that the nebulizers described above can feature spraying anomalies when using aqueous pharmaceutical solutions (generally, double distilled or demineralized (ion exchanged) water is used as a solvent). These spraying anomalies represent an alteration of the spraying pattern of the aerosol, with the consequence that in extreme cases an exact dose can no longer be guaranteed to the patient as a result of the altered mean droplet size distribution (alteration to the lung accessible part of the aerosol). These spraying anomalies especially occur when the nebulizers is used at intervals, for example, with breaks of approximately 3 or more days between utilization. It is possible that these spraying anomalies, which in extreme cases can lead to a dysfunction of the nebulizers, are as a result of microscopic deposits in the area of the jet opening.

Surprisingly, it was discovered that these spraying anomalies no longer occur when the aqueous pharmaceutical preparations which are to be sprayed contain a defined effective quantity of a complexing agent, especially of EDTA (ethylenediamine tetraacetic acid) or salts thereof. The aqueous pharmaceutical preparations according to the invention contain water as a solvent, but if necessary, ethanol can be added to increase the solubility up to 70% (by volume), preferably between 30% and 60% (by volume).

Other pharmacological adjuvants such as preservatives, especially benzalkonium chloride, can be added. The preferred quantity of preservative, especially benzalkonium chloride, is between 8 and 12 mg/100 ml solution.

Suitable complexing agents are those which are pharmacologically acceptable, especially those which are already approved by medical regulating authorities. EDTA, nitrilotriacetic acid, citric acid, and ascorbic acid and their salts are especially suitable. The disodium salt of ethylenediaminetetraacetic acid is especially preferred.

The quantity of complexing agent is selected so that an effective quantity of complexing agent is added to prevent further occurrence of spraying anomalies.

The effective quantity of the complexing agent Na-EDTA is between 10 and 1000 mg/100 ml solution, especially between 10 and 100 mg/100 ml solution. The preferred range of the quantity of complexing agent is between 25 and 75 mg/100 ml solution, especially between 25 and 50 mg/100 ml solution.

The following named compounds can principally be used as active ingredients, singly or in combination, in the aqueous pharmaceutical preparation according to the invention. In individual cases, it may be required to add a higher quantity of ethanol or a solution mediator to improve solubility.

Tiotropium bromide, 3-[(hydroxydi-2-thienylacetyl)oxy]-8,8-dimethyl-8-azoniabicyclo[3.2.1]oct-6-ene-bromide As betamimetics:

| | | | |
|---|---|---|---|
| Bambuterol | Bitolterol | Carbuterol | Formoterol |
| Clenbuterol | Fenoterol | Hexoprenaline | Procaterol |
| Ibuterol | Pirbuterol | Salmeterol | Tulobuterol |
| Reproterol | Salbutamol | Sulfonterol | Terbutaline |

1-(2-Fluoro-4-hydroxyphenyl)-2-[4-(1-benzimidazolyl)-2-methyl-2-butylamino]ethanol,
erythro-5'-hydroxy-8'-(1-hydroxy-2-isopropylaminobutyl)-2H-1,4-benzoxazin-3-(4H)-one, 1-(4-Amino-3-chloro-5-trifluoromethylphenyl)-2-tert.-butyl-amino)ethanol, and
1-(4-Ethoxycarbonylamino-3-cyano-5-fluorophenyl)-2-(tert.-butylamino)ethanol.

As Anticholinergics:
Ipratropium bromide, Oxitropium bromide, Trospium chloride, and N-β-fluoroethylene nortropine benzylate methobromide As Steroids:
Budesonide, Beclometasone (or the 17,21-dipropionate), Dexamethasone-21-isonicotinate, and Flunisolide As Antiallergics:
Disodium cromoglycate, Nedocromil, and Epinastine.

Examples of Steroids which can be Used as Active Ingredients in the Pharmaceutical Preparations According to the Invention:

| | |
|---|---|
| Seratrodast | Mycophenolate mofetil |
| Pranlukast | Zileutone |
| Butixocort | Budesonide |
| Deflazacort | |
| Fluticasone | Promedrol |
| Mometasone furoate | Tipredane |
| Beclometasone, Douglas | Icomethasone enbutate |
| Ciclometasone | Cloprednol |
| Fluocortin butyl | Halometasone |
| Deflazacort | Alclometasone |
| Ciclometasone | Alisactide |
| Prednicarbate | Hydrocortisone-butyrate propionate |
| Tixocortol-pivalate | Alclometasone-dipropionate |
| Lotrisone | Canesten-HC |
| Deprodone | Fluticasone-propionate |
| Methylprednisolone-Aceponate | Halopredone-acetate |
| Mometasone | Mometasone-furoate |
| Hydrocortisone-aceponate | Mometasone |
| Ulobetasol-propionate | Aminoglutethimide |
| Triamcinolone | Hydrocortisone |
| Meprednisone | Fluorometholone |
| Dexamethasone | Betamethasone |
| Medrysone | Fluclorolone acetonide |
| Fluocinolone acetonide | Paramethasone-acetate |
| Deprodone Propionate | Aristocort-diacetate |
| Fluocinonide | Mazipredone |
| Difluprednate | Betamethasone valerate |
| Dexamethasone isonicotinate | Beclomethasone-Dipropionate |
| Fluocortolone capronate | Formocortal |
| Triamcinolone-Hexacetonide | Cloprednol |
| Formebolone | Clobetasone |
| Endrisone | Flunisolide |
| Halcinonide | Fluazacort |
| Clobetasol | Hydrocortisone-17-Butyrate |
| Diflorasone | Fluocortin |
| Amcinonide | Betamethasone Dipropionate |
| Cortivazol | Betamethasone adamantoate |
| Fluodexane | Trilostane |
| Budesonide | Clobetasone |
| Demetex | Trimacinolon Benetonide | and 9-α-chloro-6-α-fluoro-11-β-17-α-dihydroxy-16-α-methyl-3-oxo-1,4-androstadiene-17-β-carboxylic acid-methylester-17-propionate.

Other especially suitable active ingredients for the production of aqueous pharmaceutical preparations for applications by inhalation are:

β-Sympatico-mimetics, e.g. Fenoterol, Salbutamol, Formoterol, or Terbutalin;
Anticholinergics, e.g. Ipratropium, Oxitropium, or Tiotropium;
Steroids, e.g., Beclomethasone dipropionate, Budesonide, or Flunisolide;
Peptides, e.g., insulin; and
Pain killers, e.g., Fentanyl.

It is obvious that those pharmacologically acceptable salts will be used which dissolve in the solvent according to the invention if necessary.

In the following text, the advantage of the pharmaceutical preparation according to the invention will be explained more clearly with Examples.

As a pharmaceutical solution, Ipratropium bromide solution (c=333 mg/100 ml) with a pH value of 3.4, and the preservative benzalkonium chloride (c=10 mg/100 ml) was used. The tested solutions either contained no EDTA or EDTA in a concentration of c=0.1 mg, 1 mg, 50 mg and 75 mg/100 ml as a disodium salt.

Unused Respimat® nebulizers were used for the test (technical data: volumes of the applied pharmaceutical preparation approximately 15 μl, pressure approximately 300 bar, 2 streams impacting from two jet openings of size 5×8 μm). The operation mode for the test is set so that the units are used 5 times, are left to stand for 3 days, and then are used again 5 times, this pattern being repeated. 15 units were examined in each series of measurements, the results with regard to spray anomalies are shown in Table 1.

TABLE 1

| Test No. | Concentration of EDTA in mg/100 ml | Number of nebulizers with spray anomalies | Duration of test in days |
|---|---|---|---|
| 1 | 0 mg/100 ml | 2 | 20 |
| 2 | 0 mg/100 ml | 5 | 9 |
| 3 | 0.1 mg/100 ml | 5 | 6 |
| 4 | 1 mg/100 ml | 6 | 6 |
| 5 | 50 mg/100 ml | 0 | 200 |
| 6 | 50 mg/100 ml | 0 | 200 |
| 7 | 75 mg/100 ml | 0 | 200 |
| 8 | 75 mg/100 ml | 0 | 200 |

Formulation Examples (for Fenoterol and Ipatropium bromide)

| Components | Composition in mg/100 ml |
|---|---|
| Fenoterol | 833.3 mg |
| Benzalkonium chloride | 10.0 mg |
| EDTA* | 50.0 mg |
| HCl (1n) | ad pH 3.2 |
| Ipratropium bromide | 333.3 mg |
| Benzalkonium chloride | 10.0 mg |
| EDTA* | 50.0 mg |
| HCl (1N) | ad pH 3.4 |

In analogy to the above Examples, the following solutions were produced.

| Active ingredient | Concentration mg/100 ml | Benzalkonium chloride | EDTA* | Solvent |
|---|---|---|---|---|
| Berotec | 104-1.667 | 10 mg | 50 mg | Water |
| Atrovent | 83-1.333 | 10 mg | 50 mg | Water |
| Berodual | | | | |
| (Atrovent) | 41-667 | 10 mg | 50 mg | Water |
| (Berotec) | 104-1.667 | 10 mg | 50 mg | Water |
| Salbutamol | 104-1.667 | 10 mg | 50 mg | Water |
| Combivent | | | | |
| (Atrovent) | 167-667 | 10 mg | 50 mg | Water |
| (Salbutamol) | 833-1.667 | 10 mg | 50 mg | Water |
| Ba 679 Br (Tiotropium- | 4-667 | 10 mg | 50 mg | Water |

-continued

| Active ingredient | Concentration mg/100 ml | Benzalkonium chloride | EDTA* | Solvent |
|---|---|---|---|---|
| bromide) | | | | |
| BEA 2108 Br | 17-833 | 10 mg | 50 mg | Water |
| Oxivent | 416-1.667 | 10 mg | 50 mg | Water |

*In the form of the disodium salt

A concentration range from 10 mg to 20,000 mg/100 ml is conceivable for the active ingredients, depending on the dose per operation and their solubility. The specified doses are calculated based on a therapeutically effective single dose of approximately 12 microliters per operation. The active ingredient concentrations of the pharmaceutical preparations can alter when the volume of the individual dose is altered.

The concentration range for the complexing agents (for example DiNa-EDTA) is between 10 and 1000 mg/100 ml (dependent on the pH value of the solution). The preferred range is between 25 mg and 100 mg/100 ml.

The quantity of benzalkonium chloride should be in the range of 8 to 12 mg/100 ml.

The solutions are set to a pH of 3.2 to 3.4 with 0.1 or 1N HCl. All concentrations relate to 100 ml of finished active ingredient solution.

We claim:

1. A method of providing defined volumes of an aqueous pharmaceutical solution comprising a pharmacologically active ingredient and an effective quantity of a complexing agent for the prevention of spraying anomalies as a propellant-free aerosol for inhalation, the method comprising:

(a) pressurizing the pharmaceutical solution; and (b) passing the pressurized pharmaceutical solution through an atomizing means to provide defined volumes of the pharmaceutical solution as a propellant-free aerosol.

2. The method according to claim 1, wherein the pharmacologically active ingredient is selected from the group consisting of: betamimetics, anticholinergics, antiallergenics, and antihistamines.

3. The method according to claim 1, wherein the pharmacologically active ingredient is selected from the group consisting of: fenoterol, ipratropium bromide, salbutamol, tiotropium bromide, and oxitropium bromide.

4. The method according to claim 3, wherein the pharmaceutical solution further comprises an adjuvant.

5. The method according to claim 4, wherein the adjuvant is a preservative.

6. The method according to claim 5, wherein the adjuvant is benzalkonium chloride.

7. The method according to claim 1, wherein the method is accomplished using a Weston Nebulizer.

8. The method according to claim 1, wherein the method is accomplished using a Jaeger Nebulizer A.

9. The method according to claim 1, wherein the method is accomplished using a Jaeger Nebulizer B.

10. The method according to any one of claims 1 to 3 or 7 to 9, wherein the complexing agent is nitriloacetic acid, citric acid, ascorbic acid, or a salt thereof.

11. The method according to any one of claims 1 to 3 or 7 to 9, wherein the complexing agent is EDTA or a salt thereof.

12. The method according to claim 11, wherein the concentration of the complexing agent is between 25 and 75 mg/100 ml solution.

13. The method according to any one of claims 1 to 3 or 7 to 9, wherein the pharmaceutical solution contains up to 70% (by volume) ethanol.

14. The method according to any one of claims 1 to 3 or 7 to 9, wherein the pharmaceutical solution contains the pharmacologically active ingredient in a concentration of 0.001 to 2 g/100 ml solution.

15. The method according to claim 2, wherein the pharmacologically active ingredient is selected from the group consisting of: fenoterol, ipratropium bromide, salbutamol, tiotropium bromide, and oxitropium bromide.

16. The method according to claim 1, wherein the pharmaceutical solution further comprises an adjuvant.

17. The method according to claim 16, wherein the adjuvant is a preservative.

18. The method according to claim 17, wherein the preservative is benzalkonium chloride.

* * * * *